United States Patent
Hayashi

(10) Patent No.: US 9,824,443 B2
(45) Date of Patent: Nov. 21, 2017

(54) IMAGE PROCESSING DEVICE, IMAGE PROCESSING METHOD, AND PROGRAM

(71) Applicant: SONY CORPORATION, Tokyo (JP)

(72) Inventor: Tsuneo Hayashi, Chiba (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 14/914,780

(22) PCT Filed: Jul. 24, 2014

(86) PCT No.: PCT/JP2014/069617
§ 371 (c)(1),
(2) Date: Feb. 26, 2016

(87) PCT Pub. No.: WO2015/037340
PCT Pub. Date: Mar. 19, 2015

(65) Prior Publication Data
US 2016/0203602 A1    Jul. 14, 2016

(30) Foreign Application Priority Data
Sep. 10, 2013    (JP) ................ 2013-187248

(51) Int. Cl.
*G06K 9/00*        (2006.01)
*G06T 7/00*        (2017.01)
(Continued)

(52) U.S. Cl.
CPC ........ *G06T 7/0012* (2013.01); *A61B 1/00009* (2013.01); *A61B 1/00193* (2013.01);
(Continued)

(58) Field of Classification Search
CPC ..... G06T 7/0012; G06T 7/0081; G06T 11/60; A61B 1/00009; A61B 1/00193;
(Continued)

(56) References Cited

U.S. PATENT DOCUMENTS 5,748,296 A * 5/1998 Canteloup .......... G01B 11/0675
                                                    257/E21.53
8,933,964 B2 * 1/2015 Yamada ................. H04N 7/183
                                                    345/619
(Continued)

FOREIGN PATENT DOCUMENTS

CN    102949172 A    3/2013
JP    2008-136671 A  6/2008
(Continued)

OTHER PUBLICATIONS

International Search Report dated Nov. 11, 2014 in PCT/JP2014/069617 (with English translation).
(Continued)

*Primary Examiner* — Shefali Goradia
(74) *Attorney, Agent, or Firm* — Oblon, McClelland, Maier & Neustadt, L.L.P.

(57) ABSTRACT

[Object] To improve work efficiency with respect to work using a transparent object, such as a transparent operation tool, for example.
[Solution] An image region where an object exists as a target region is detected on the basis of a second captured image, when a first captured image is a captured image obtained by selectively receiving a light of a first wavelength band, and the second captured image is a captured image obtained by selectively receiving a light of a second wavelength band, the captured images being obtained by capturing the object that is transparent for the light of the first wavelength band and is opaque for the light of the second wavelength band. Subsequently, an outline of the object is superimposed on the first captured image on the basis of information of the target region detected by the target detecting unit.

13 Claims, 12 Drawing Sheets

(51) Int. Cl.
  *A61B 1/06* (2006.01)
  *A61B 3/14* (2006.01)
  *G06K 9/32* (2006.01)
  *G06K 9/62* (2006.01)
  *G06T 11/60* (2006.01)
  *H04N 5/225* (2006.01)
  *H04N 13/02* (2006.01)
  *A61B 1/00* (2006.01)

(52) U.S. Cl.
  CPC .............. *A61B 1/0638* (2013.01); *A61B 3/14* (2013.01); *G06K 9/3241* (2013.01); *G06K 9/6202* (2013.01); *G06T 7/0081* (2013.01); *G06T 11/60* (2013.01); *H04N 5/225* (2013.01); *H04N 13/0225* (2013.01); *H04N 2005/2255* (2013.01)

(58) Field of Classification Search
  CPC ...... A61B 3/14; G06K 9/3241; G06K 9/6202; H04N 5/225; H04N 13/0225; H04N 2005/2255
  See application file for complete search history.

(56) References Cited

U.S. PATENT DOCUMENTS

2013/0002844 A1  1/2013  Shida
2013/0044126 A1  2/2013  Yamada

FOREIGN PATENT DOCUMENTS

WO    WO 2011/118287 A1    9/2011
WO    WO 2013/015120 A1    1/2013

OTHER PUBLICATIONS

Extended European Search Report dated Mar. 6, 2017 in Patent Application No. 14843857.5.

Office Action issued in corresponding Chinese Application No. 2014800486499, dated May 24, 2013 (with English translation).

\* cited by examiner

| OPERATION TOOL ID | OPTICAL DISTORTION CHARACTERISTIC INFORMATION |
|---|---|
| ID1 | H1 |
| ID2 | H2 |
| ID3 | H3 |
| ⋮ | ⋮ |
| IDn | Hn |

| OPERATION TOOL ID | ORIENTATION | OPTICAL DISTORTION CHARACTERISTIC INFORMATION |
|---|---|---|
| ID1 | P1 | H1p1 |
|  | P1 | H1p2 |
|  | ⋮ | ⋮ |
|  | Pm | H1pm |
| ⋮ | ⋮ | ⋮ |
| IDn | P1 | Hnp1 |
|  | P1 | Hnp2 |
|  | ⋮ | ⋮ |
|  | Pm | Hnpm |

IMAGE PROCESSING DEVICE, IMAGE PROCESSING METHOD, AND PROGRAM

TECHNICAL FIELD

The present technology relates to a technology field of an image processing device, an image processing method, and a program that perform image processing for a captured image obtained by capturing an image of a visible light transparent object, such as a transparent operation tool for example.

CITATION LIST

Patent Literature

Patent Literature 1: JP 2009-291358A
Patent Literature 2: JP 2011-35853A

BACKGROUND ART

What is called a minimally invasive surgical operation for reducing a physical burden on a patient is known. In the minimally invasive surgical operation, a surgeon performs a surgical operation while confirming an internal body image captured by an endoscope, in order to perform the surgical operation without opening a chest or an abdomen and to reduce a physical burden on the patient in the surgical operation.

SUMMARY OF INVENTION

Technical Problem

When the surgical operation is performed by using the endoscope as in the minimally invasive surgical operation, it is conceived to use a transparent operation tool, such as a scalpel and a forceps, as an operation tool. If the operation tool is transparent, the visibility of an observation object, such as an organ, positioned at a deeper side improves desirably.

However, if the transparent operation tool is used, it is difficult for a viewer, such as a surgeon, to confirm the position of the operation tool in the captured image, and it is concerned that the surgical operation becomes more difficult.

Thus, a purpose of the present technology is to overcome the above problem, and to improve work efficiency with respect to work using a transparent object, such as a transparent operation tool, for example.

Solution to Problem

First, according to the present technology, an image processing device includes: a target detecting unit configured to detect an image region where an object exists as a target region on the basis of a second captured image, when a first captured image is a captured image obtained by selectively receiving a light of a first wavelength band, and the second captured image is a captured image obtained by selectively receiving a light of a second wavelength band, the captured images being obtained by capturing the object that is transparent for the light of the first wavelength band and is opaque for the light of the second wavelength band; and an outline superimposing unit configured to superimpose an outline of the object on the first captured image on the basis of information of the target region detected by the target detecting unit.

As described above, the captured image in which the deeper side of the object is visually confirmable and the position of the object is visually confirmable is obtained by superimposing the outline of the object on the first captured image.

Second, in the image processing device according to the present technology, the target detecting unit detects the target region on the basis of the second captured image and the first captured image, preferably. Thereby, the target region is detected on the basis of the image displaying the object transparently and the image displaying the object opaquely.

Third, in the image processing device according to the present technology, the target detecting unit preferably generates a second edge image based on the second captured image and a first edge image based on the first captured image by performing an edge extraction with respect to each of the second captured image and the first captured image, performs a template matching using a template of the object for each of the second edge image and the first edge image, and detects, as the target region, an image region that is detected by the template matching for the second edge image and does not overlap with an image region detected by the template matching for the first edge image. Thereby, the image region erroneously detected in the template matching for the second captured image can be excluded.

Fourth, in the image processing device according to the present technology, the target detecting unit preferably performs the edge extraction with respect to the second captured image and a plurality of first captured images obtained by selectively receiving lights of different wavelength bands in the first wavelength band, and generates the second edge image based on the second captured image and a plurality of first edge images based on the plurality of first captured images, performs the template matching for each of the generated edge images, and detects, as the target region, an image region that is detected by the template matching for the second edge image and does not overlap with any one of image regions detected by the template matching for the plurality of first edge images. The part other than the object having the similar shape as the object is detected more easily in the visible light image side, by performing the template matching for a plurality of first captured images obtained by selectively receiving lights of the different wavelength bands in the first wavelength band.

Fifth, in the image processing device according to the present technology, when a left eye side second captured image and a right eye side second captured image are a left eye image and a right eye image obtained by stereoscopically capturing images of the object by means of an image sensor that selectively receives a light of the second wavelength band, respectively, the target detecting unit detects the target region on the basis of distance information calculated on the basis of a parallax between the left eye side second captured image and the right eye side second captured image, preferably. As described above, the target region can be detected by using the distance information.

Sixth, in the image processing device according to the present technology, the target detecting unit generates a distance image of the second captured image and a distance image of the first captured image on the basis of the distance information calculated with respect to each of the second captured image and the first captured image, generates a difference image between the distance image of the second captured image and the distance image of the first captured image, and detects the target region on the basis of the difference image, preferably. As described above, only the image region that the object exists is extracted in the difference image, by generating the difference image between the distance image of the second captured image and the distance image of the first captured image.

Seventh, in the image processing device according to the present technology, the target detecting unit decides the target region used in superimposition of the outline by the outline superimposing unit, on the basis of a detection result of the target region with respect to a plurality of frame images, preferably. Thereby, even if the part displaying the matter other than the object is erroneously detected as the target region due to influence such as temporary noise, the influence is not reflected in outline superimposition.

Eighth, the image processing device according to the present technology preferably includes an optical distortion correcting unit configured to correct an optical distortion generated by the object with respect to the target region in the first captured image. Thereby, the optical distortion generated in the target region in the first captured image is corrected.

Ninth, in the image processing device according to the present technology, the target detecting unit preferably identifies a type of the object on the basis of the second captured image, and the optical distortion correcting unit preferably corrects the optical distortion with a correction characteristic according to the type of the object identified by the target detecting unit. Thereby, the optical distortion correction is performed by the appropriate correction characteristic according to the type of the object.

Tenth, in the image processing device according to the present technology, when a left eye side second captured image and a right eye side second captured image are a left eye image and a right eye image obtained by stereoscopically capturing images of the object by means of an image sensor that selectively receives a light of the second wavelength band, respectively, the target detecting unit generates three-dimensional position information of the object on the basis of the left eye side second captured image and the right eye side second captured image, and detects an orientation of the object on the basis of the three-dimensional position information, and the optical distortion correcting unit corrects the optical distortion with a correction characteristic according to the orientation of the object detected by the target detecting unit, preferably. Thereby, the optical distortion correction is performed by the appropriate correction characteristic according to the orientation of the object.

Eleventh, in the image processing device according to the present technology, the optical distortion correcting unit preferably corrects the optical distortion with a correction characteristic according to a distance of the object. Thereby, the optical distortion correction is performed by the appropriate correction characteristic according to the distance of the object.

Advantageous Effects of Invention

According to the present technology, the work efficiency is improved with respect to the work using the transparent object, such as the transparent operation tool for example. Note that the effect described herein is not necessarily restrictive, but may be one of the effects described in the present disclosure.

BRIEF DESCRIPTION OF DRAWINGS

FIG. 6 is an explanatory diagram of information detail of an optical distortion information DB used by an image processing device of the first embodiment.

FIG. 12 is an explanatory diagram of information detail of an optical distortion information DB used by an image processing device of the third embodiment.

DESCRIPTION OF EMBODIMENTS

In the following, the embodiment is described in the next order.
<1. First Embodiment>
  (1-1. Assumption)
  (1-2. Overall Configuration of Image Capturing Device)
  (1-3. With Regard To Signal Processing Unit)
  (1-4. With Regard To Program)
  (1-5. Conclusion and Effect)
<2. Second Embodiment>
  (2-1. Configuration and Operation)
  (2-2. Conclusion and Effect)
<3. Third Embodiment>
  (3-1. Configuration and Operation)
  (3-2. Conclusion and Effect)
<4. Exemplary Variant>
<5. Present Technology>
<1. First Embodiment>
(1-1. Assumption)

Figure 1:
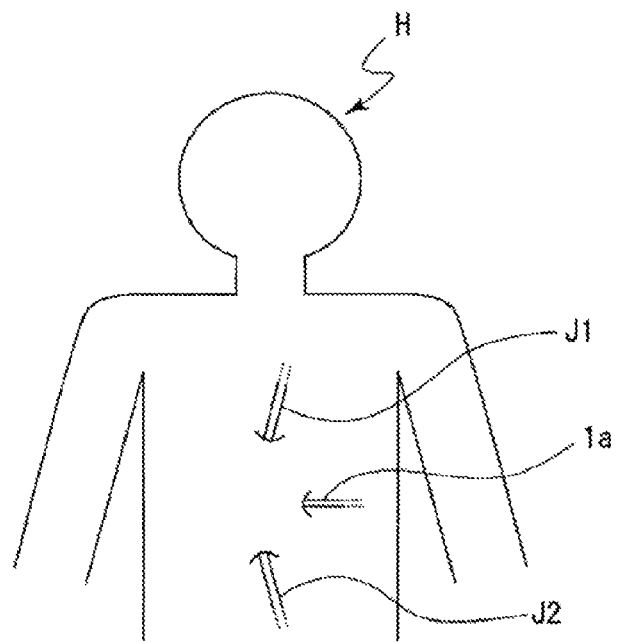
FIG. 1 is an explanatory diagram of a minimally invasive surgical operation and a transparent operation tool, which are assumed in an embodiment.
Figure 1:
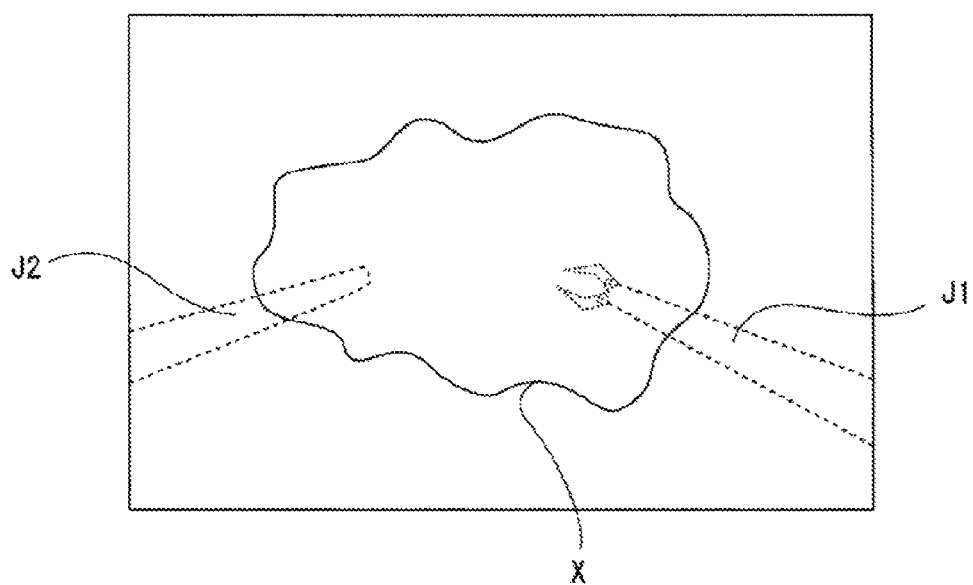

FIG. 1 is an explanatory diagram of a minimally invasive surgical operation and a transparent operation tool, which are assumed in the present embodiment. As illustrated in FIG. 1A, in the minimally invasive surgical operation which are assumed in the present embodiment, operation tools J and a rigid endoscope (an endoscope) 1a of an image capturing device 1 described later are inserted into the inside of the body of a patient H. This diagram illustrates a case in which two types of operation tools J, which are an operation tool J1 and an operation tool J2, are inserted into the inside of the body. The insertion of the operation tools J and the rigid endoscope 1a into the inside of the body is performed through minimally invasive openings made in the patient H, respectively.

The operation tools J is a surgical operation tool such as a scalpel and a forceps for example, and what is called a transparent operation tool is used in the present embodiment. The transparent operation tool means an operation tool that is transparent for a visible light.

FIG. 1B schematically illustrates a captured image obtained via the rigid endoscope 1a when the operation tools J and the rigid endoscope 1a are inserted as illustrated in FIG. 1A. In this case, although the operation tool J1 and the operation tool J2 exist at the front side of an intracorporeal object X such as an organ in the field of view of image capturing, these operation tool J1 and operation tool J2 are not displayed completely in the captured image, and the intracorporeal object X is seen through at the deeper side of each of the operation tool J1 and the operation tool J2, because these operation tool J1 and operation tool J2 are transparent operation tools.

Although the deeper side of the operation tools J is seen through to improve visibility of the intracorporeal object X and to improve the easiness of the surgical operation, the position of the transparent operation tool is difficult to confirm in the captured image as described above, and it is concerned that the surgical operation becomes more difficult.

Thus, in the present embodiment, a captured image that makes the deeper side of the operation tools J visually confirmable and the positions of the operation tools J visually confirmable is provided, in order to improve the work efficiency with respect to the surgical operation work using the transparent operation tool, and improve the easiness of the surgical operation.

Hence, in the present embodiment, operation tools that are transparent for a visible light and are opaque for an infrared light are used as the operation tools J. Specifically, the operation tools J in the present example are covered by a film that transmits a visible light but reflects or absorbs an infrared light. For example, this film is "Multi Layer Nano Series" made by 3M Company or the like. Note that the operation tools J can be made of a glass material that transmits a visible light but reflects or absorbs an infrared light. For example, this glass is the product illustrated in the below web page (produced by Central Glass Co., Ltd.) or the like.

http://www.cg-glass.jp/pro/sub_technique/pdf/180-181.pdf (1-2. Overall Configuration of Image Capturing Device)

Figure 2:
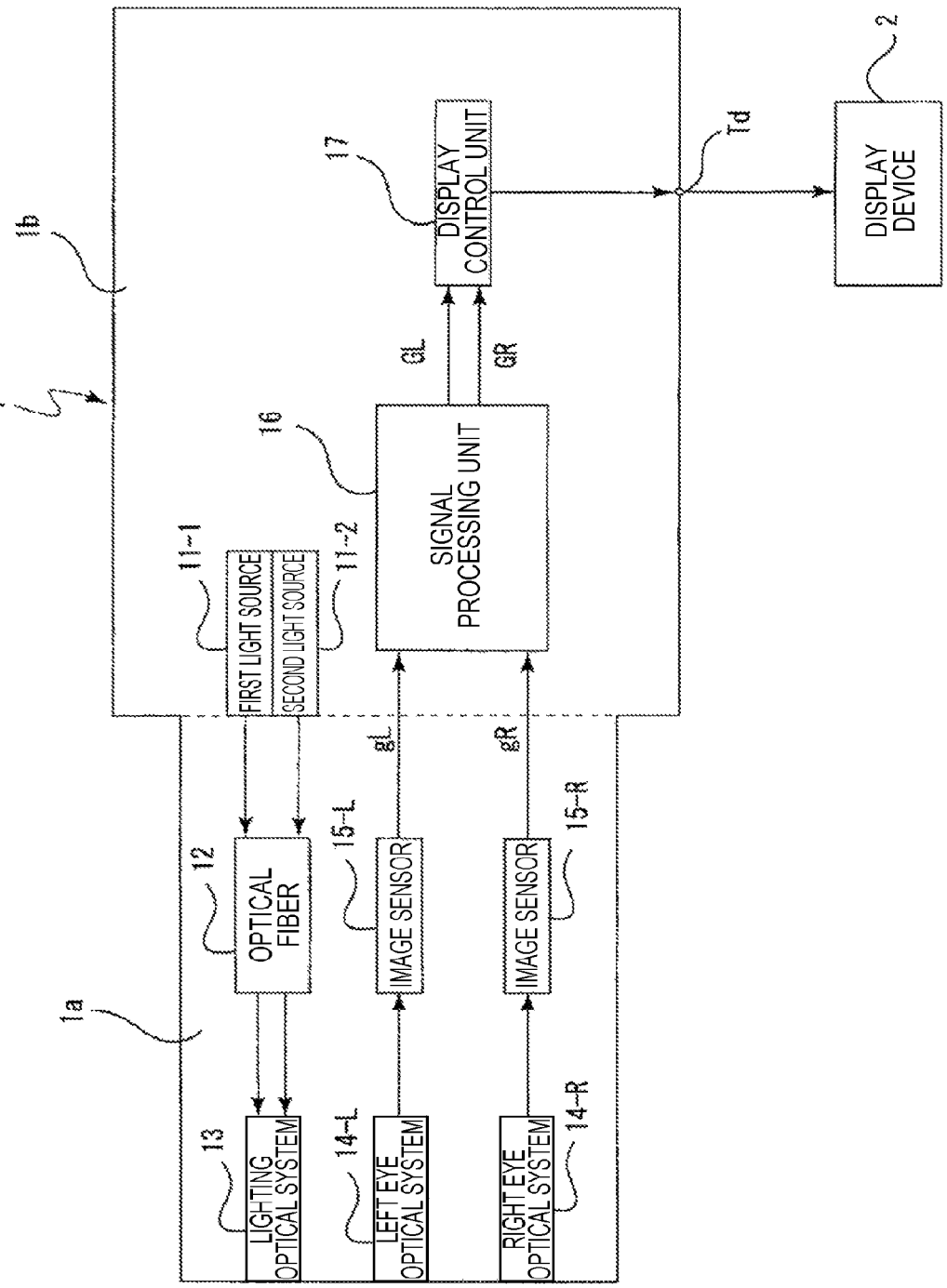
FIG. 2 is a block diagram for describing an inner configuration of an image capturing device of a first embodiment.

FIG. 2 is a block diagram illustrating an inner configuration of the image capturing device 1 as the first embodiment. Note that FIG. 1 also illustrates a display device 2 for displaying a captured image obtained by the image capturing device 1. The image capturing device 1 is an image capturing device configured with an image processing device as the first embodiment.

The image capturing device 1 includes a rigid endoscope 1a and a main body 1b. In the rigid endoscope 1a, an optical fiber 12, a lighting optical system 13, a left eye optical system 14-L, a right eye optical system 14-R, an image sensor 15-L, and an image sensor 15-R are provided. In the main body 1b, a first light source 11-1, a second light source 11-2, a signal processing unit 16, a display control unit 17, and a terminal Td are provided.

The first light source 11-1 emits a visible light. In the case of the present example, the first light source 11-1 emits a white light. The second light source 11-2 emits an infrared light.

Both of the visible light emitted from the first light source 11-1 and the infrared light emitted by the second light source 11-2 enter into the lighting optical system 13 through the optical fiber 12. The lighting optical system 13 projects the visible light and the infrared light that have entered via the optical fiber 12, on a subject as an observation target.

The left eye optical system 14L and the right eye optical system 14R are provided to generate a left eye image GL and a right eye image GR for presenting a stereoscopic viewing image. The left eye optical system 14L collects the light from the subject to form an image on an imaging capturing surface of the image sensor 15-L. The right eye optical system 14-R collect the light from the subject to form an image on an imaging capturing surface of the image sensor 15-R.

Figure 3:
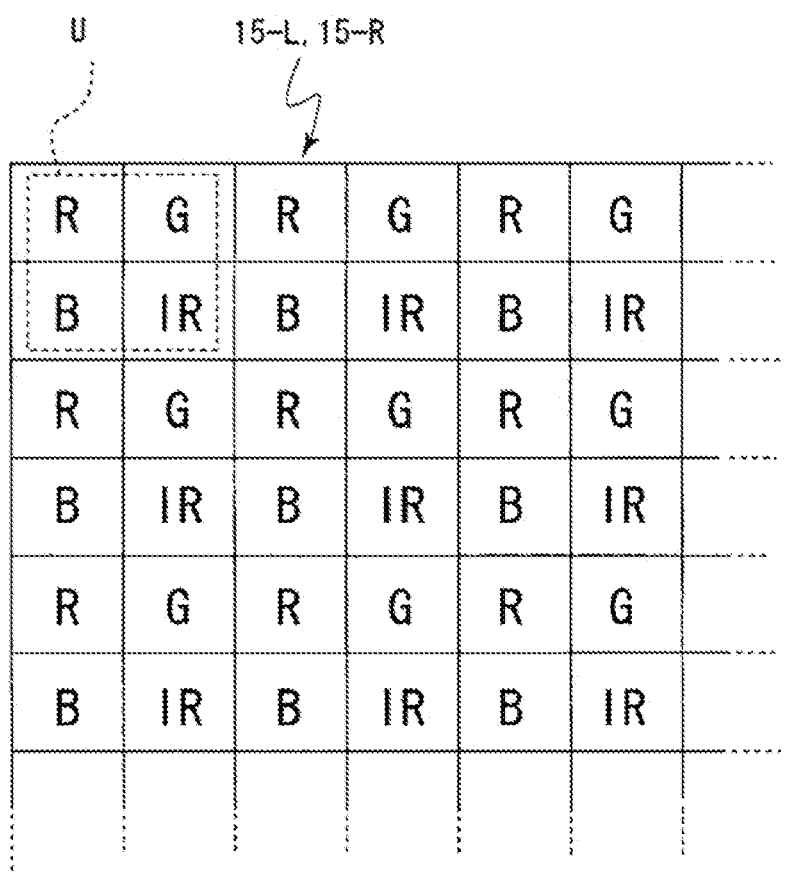
FIG. 3 is an explanatory diagram of a structure of an image sensor included in an image capturing device of the first embodiment.

In the present example, the image sensor 15-L and the image sensor 15-R have a structure illustrated in FIG. 3 to enable simultaneous light reception of the visible light and the infrared light. In each of the image sensor 15-L and the image sensor 15-R, one unit U is composed of total 4 pixels including 2 pixels in the horizontal direction×2 pixels in the vertical direction. In this case, the unit U includes a pixel at which a wavelength filter that selectively transmits a red light is formed (represented by "R" in the drawing), a pixel at which a wavelength filter that selectively transmits a green light is formed (represented by "G" in the drawing), a pixel at which a wavelength filter that selectively transmits a blue light is formed (represented by "B" in the drawing), and a pixel at which a wavelength filter that selectively transmits an infrared light is formed (represented by "IR" in the drawing). In the image sensor 15-L and the image sensor 15-R, a plurality of units U are arrayed in the horizontal direction and the vertical direction. Thereby, in each of the image sensor 15-L and the image sensor 15-R, the red light, the green light, the blue light, and the infrared light are received selectively at different positions on the imaging capturing surface.

Returning to FIG. 2, a captured image signal obtained by the image sensor 15-L is represented by "captured image signal gL", and a captured image signal obtained by the image sensor 15-R is represented by "captured image signal gR". The captured image signal gL and the captured image signal gR are input into the signal processing unit 16.

The signal processing unit 16 generates a left eye image GL on the basis of the captured image signal gL, and a right eye image GR on the basis of the captured image signal gR, respectively. The signal processing unit 16 corresponds to the image processing device of the first embodiment, and its inner configuration will be described later.

The display control unit 17 performs a control to cause the display device 2, which is connected via the terminal Td, to display the left eye image GL and the right eye image GR in a stereoscopic viewing manner. In the present example, the display device 2 is a display that presents a stereoscopic viewing image by a lenticular method for example, and the display control unit 17 performs a display control corresponding to the lenticular method.

(1-3. With Regard to Signal Processing Unit)

Figure 4:
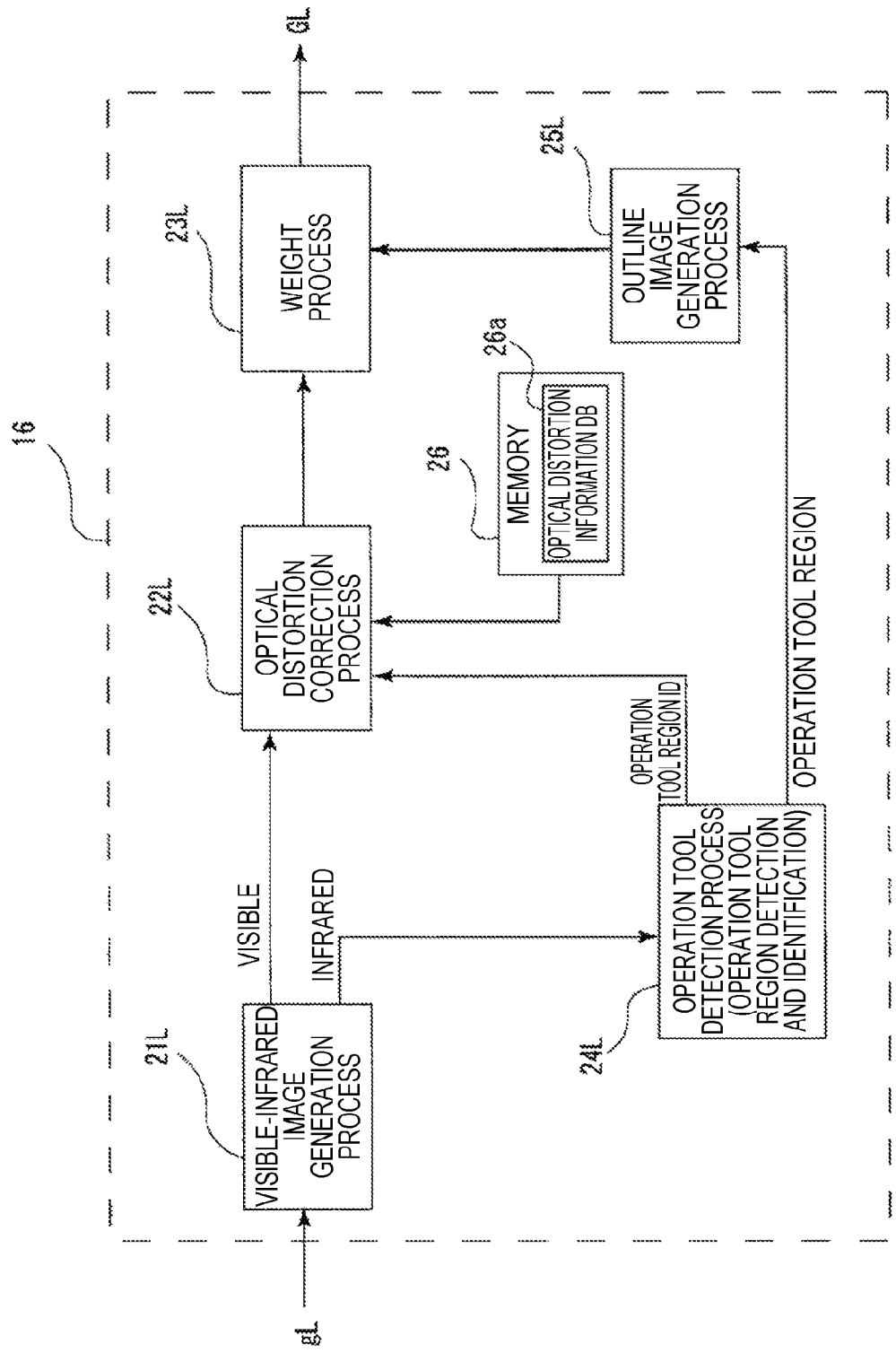
FIG. 4 is a block diagram for describing an inner configuration of a signal processing unit (an image processing device) included in an image capturing device of the first embodiment.

FIG. 4 is a block diagram for describing an inner configuration of the signal processing unit 16. Although this diagram extracts and illustrates only the configuration for the generation of the left eye image GL in the inner configuration of the signal processing unit 16, the configuration for the generation of the left side image GL is same as the configuration for the generation of the right eye image GR, and thus the depiction of the configuration for the generation of the right eye image GR is omitted to avoid a repetitive description here.

In the signal processing unit 16, a visible-infrared image generation processing unit 21L, an optical distortion correction processing unit 22L, a superimposition processing unit 23L, an operation tool detection processing unit 24L, an outline image generation processing unit 25L, and a memory 26 are provided.

The visible-infrared image generation processing unit 21L generates the visible light image and the infrared light image, on the basis of the captured image signal gL input from the image sensor 15-L. In the case of the present example, the visible light image is a color image including brightness values of red light, green light, blue light for each pixel. The infrared light image is an image including a brightness value of infrared light for each pixel. The visible-infrared image generation processing unit 21L generates the visible light image and the infrared light image by performing a demosaic process for the captured image signal gL. With respect to a pixel at an i-th position in the horizontal direction and a j-th position in the vertical direction on the image sensor 15-L, the demosaic process interpolates (for example, linear interpolation, etc.) the brightness value of each of other wavelength bands other than the wavelength band received via the wavelength filter of the pixel, using brightness values of pixels formed with the wavelength filter that transmits the light of the same wavelength bands located at the vicinity of the pixel. For example, if the pixel (i, j) is a pixel that receives a red light, the brightness values of green, blue, infrared light other than red are interpolated by using brightness values of pixels formed with the wavelength filters that transmit lights of the same wavelength bands positioned at the vicinity of the pixel (i, j). Brightness values of red light, green light, blue light, and infrared light are acquired for each pixel by this demosaic process. The visible-infrared image generation processing unit 21L outputs an image having brightness values of red light, green light, and blue light for each pixel, as a visible light image. Also, the visible-infrared image generation processing unit 21L outputs an image having a brightness value of infrared light for each pixel, as an infrared light image.

The visible light image output from the visible-infrared image generation processing unit 21L is output to the display control unit 17 illustrated in FIG. 1 as the left eye image GL via the optical distortion correction processing unit 22L and the superimposition processing unit 23L. Note that the optical distortion correction processing unit 22L and the superimposition processing unit 23L will be described later.

On the other hand, the infrared light image output from the visible-infrared image generation processing unit 21L is input into the operation tool detection processing unit 24L. The operation tool detection processing unit 24L detects an image region in which the operation tools J exist, as an operation tool regions Aj, on the basis of the input infrared light image. Also, the operation tool detection processing unit 24L identifies the types of the operation tools J.

The operation tool detection processing unit 24L of the present embodiment performs detection of the operation tool regions Aj and identification of the types of the operation tools J, as in the following. First, edge extraction (edge detection) is performed for the input infrared light image. Thereafter, the operation tool regions Aj are detected by template matching, from the image after edge extraction. That is, an image region having an edge shape whose degree of similarity to the edge shape represented in the templates of the operation tools J is equal to or larger than a predetermined value is detected as the operation tool region Aj. The template matching in this case is based on the entire shape (outline) of the operation tool J, or based on the feature shapes of a part of the operation tool J, for example. In the case of the present example, a plurality of types of operation tools J are assumed to be used, and therefore the above template is prepared for each type of the operation tools J, and the matching is performed by using all of those templates, in order to detect the operation tool regions Aj.

Note that, when it is assumed that the positions of the operation tools J change in the depth direction (the direction in parallel with the image capturing direction), that is, when it is assumed that the sizes of the operation tools J are different in the captured image, a plurality of templates of different scale sizes may be prepared as the template, and the operation tool regions Aj may be detected by performing a matching using each of those templates.

In the case of the present embodiment, information of an operation tool ID that indicates the types of an operation tool J is linked to each template. The operation tool detection processing unit 24L identifies the types of the operation tools J with respect to the detected operation tool regions Aj, by acquiring the operation tool IDs linked to the templates used when detecting the operation tool regions Aj.

Information of the operation tool regions Aj detected by the operation tool detection processing unit 24L is input into the outline image generation processing unit 25L. The outline image generation processing unit 25L generates an outline image representing the outlines Sj of the operation tool regions Aj, and outputs it to the superimposition processing unit 23L.

The superimposition processing unit 23L superimposes the outline image input from the outline image generation processing unit 25L, on the visible light image input via the optical distortion correcting unit 22L.

Figure 5:
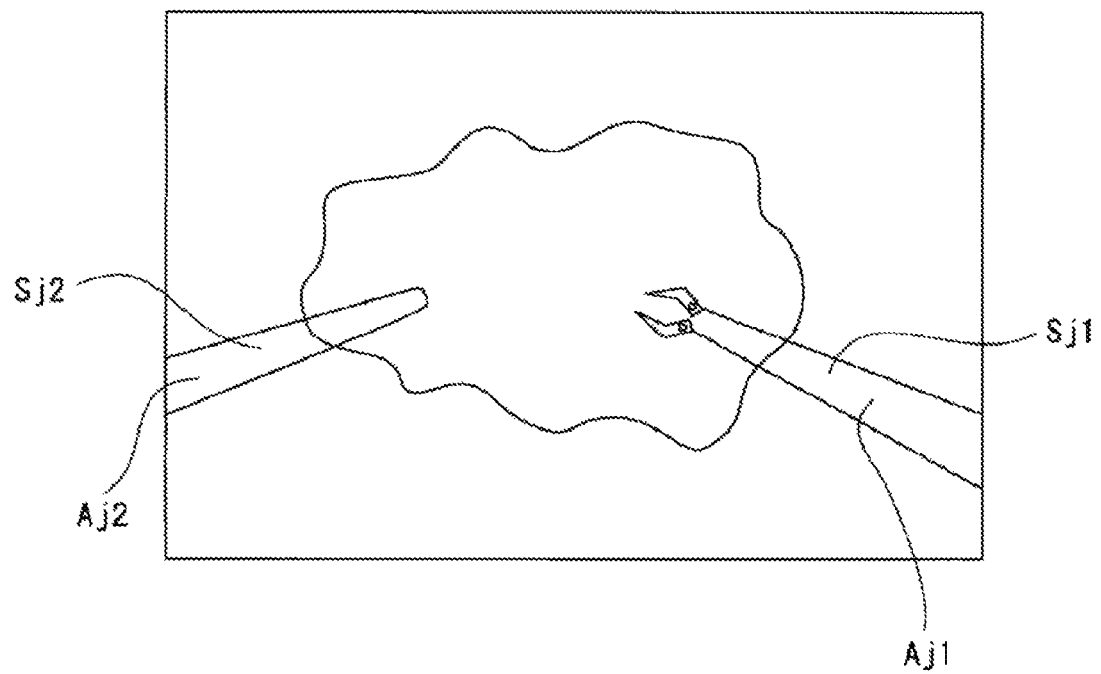
FIG. 5 is a diagram illustrating a visible light image after an outline image is superimposed.

FIG. 5 illustrates the visible light image after the outline image is superimposed by the superimposition processing unit 23L. FIG. 5 illustrates a case in which the operation tool J1 and the operation tool J2 exist in the field of view of image capturing. In this case, an operation tool region Aj1 which is an image region in which the operation tool J1 exists and an operation tool region Aj2 which is an image region in which the operation tool J2 exists are detected as the operation tool regions Aj. Then, the outline images representing the outlines (in the drawing, Sj1, Sj2) of these operation tool region Aj1 and operation tool region Aj2 are generated as outline images, and the outline images are superimposed on the visible light image.

Here, as the operation tools J is transparent for a visible light as described above, the intracorporeal object X is seen through at the deeper side of the operation tools J in the visible light image. On the other hand, since the above outline image is superimposed, the positions of the operation tools J are visually confirmed in the visible light image. Thus, a captured image is obtained in which the deeper side of the operation tools J is visually confirmable and the positions of the operation tools J are visually confirmable, by superimposing the outlines of the operation tools J on the visible light image as described above.

Note that each process of the detection of the operation tool regions Aj and the identification of the types of the operation tools J by the operation tool detection processing unit 24L described above, and the generation process of the outline image by the outline image generation processing unit 25L, and the superimposition process of the outline image by the superimposition processing unit 23L are performed with respect to each frame image.

Returning to FIG. 4, the operation tool ID and the information of the operation tool regions Aj detected by the operation tool detection processing unit 24L are input into the optical distortion correction processing unit 22L. The optical distortion correction processing unit 22L performs an optical distortion correction for the operation tool region Aj in the visible light image the target, with a correction characteristic according to the type of the operation tool J. Note that the optical distortion in this case means an optical distortion generated by the operation tool J as a transparent operation tool.

Here, although visibility is improved as the deeper side of the operation tools J is seen through as described above by using the operation tools J of transparent operation tools, it is concerned that the optical distortion makes the detail of the intracorporeal object X that exists at the deeper side of the operation tools J visually unconfirmable. Thus, as described above, the optical distortion generated by the operation tools J is corrected.

The memory 26 is a memory that can be read by the optical distortion correction processing unit 22L, and an optical distortion information database (DB) 26a is stored therein. As illustrated in FIG. 6, in the optical distortion characteristic information DB 26a, optical distortion characteristic information corresponds to each operation tool ID. In the case of the present example, the optical distortion characteristic information is information that expresses an optical distortion characteristic with a function.

In FIG. 4, the optical distortion correction processing unit 22L acquires the optical distortion characteristic information that corresponds to the same operation tool ID as the input operation tool ID among the optical distortion characteristic information stored in the optical distortion information DB 26a, and performs the optical distortion correction for the operation tool regions Aj in the visible light image on the basis of the acquired optical distortion characteristic information. That is, correction is performed to cancel the optical distortion on the basis of the acquired optical distortion characteristic information. Specifically, in the present example, optical distortion correction is performed by using an inverse function of the function of the acquired optical distortion characteristic information.

The optical distortion correction is performed to improve the visibility of the intracorporeal object X positioned at the deeper side of the operation tools J. Also, according to the above optical distortion correction process, the optical distortion correction is performed by using the correction characteristic according to the types of the operation tools J.

Note that the memory 26 and the optical distortion information DB 26a can be shared with the configuration associated with the generation of the right eye image GL, which is not depicted in the drawings.

Also, the optical distortion correction process by the optical distortion correction processing unit 22L described above is performed with respect to each frame image.

(1-4. With Regard to Program)

Figure 7:
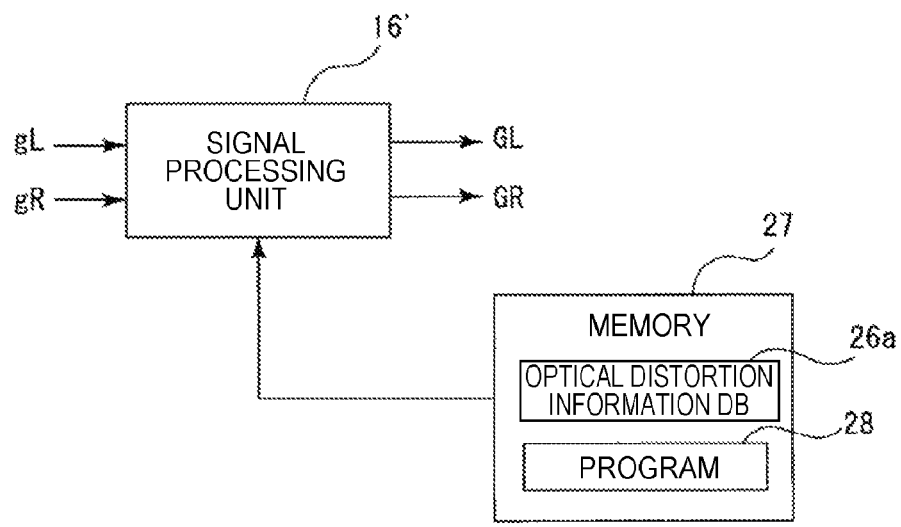
FIG. 7 is an explanatory diagram of a configuration and a process procedure when performing an operation of an image processing device according to the first embodiment by software.
Figure 7:
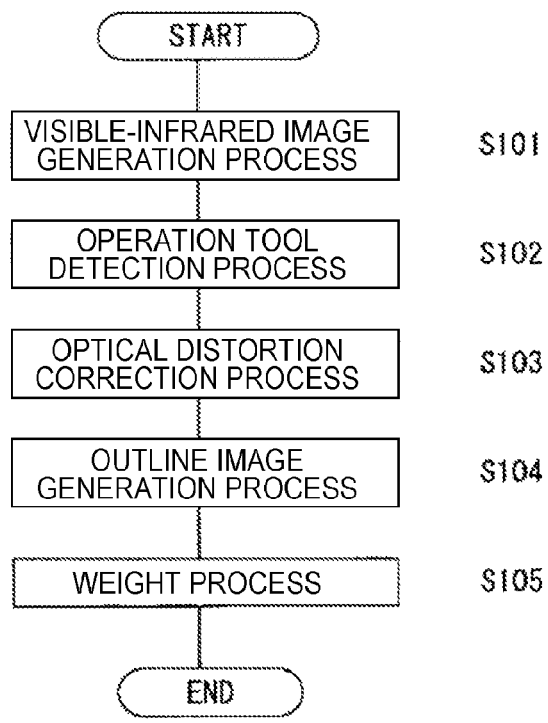

Here, although a case in which the operation of the image processing device according to the present embodiment is performed by hardware has been illustrated in the above, it may be performed by software. FIG. 7A is a diagram illustrating a configuration corresponding to the case in which the operation of the image processing device according to the present embodiment is performed by software. In this case, instead of the signal processing unit 16, a signal processing unit 16' configured with a signal processing device, such as a digital signal processor (DSP) or a microcomputer including a central processing unit (CPU) for example, is provided. A memory 27 is provided for the signal processing unit 16', and the optical distortion information DB 26a and a program 28 are stored in the memory 27. The signal processing unit 16' executes the process illustrated by the flowchart of FIG. 7B in accordance with the program 28, in order to perform the operation of the image processing device as the first embodiment.

In FIG. 7B, the signal processing unit 16' executes a visible-infrared image generation process (S101), an operation tool detection process (S102), an optical distortion correction process (S103), an outline image generation process (S104), and a superimposition process (S105). In the visible-infrared image generation process, a visible light image and an infrared light image are generated by performing the same process as the visible-infrared image generation processing unit 21L with respect to each of the input captured image signal gL and the captured image signal gR.

In the operation tool detection process, the detection of the operation tool regions Aj and the identification of the types of the operation tools J are performed by performing the same process as the operation tool detection processing unit 24L, with respect to each of the infrared light images generated from the captured image signal gL and the captured image signal gR (the infrared light image of the left eye side, the infrared light image of the right eye side).

In the optical distortion correction process, the optical distortion correction is performed for the operation tool regions Aj detected in the operation tool detection process, depending on the types of the operation tools J on the basis of the operation tool ID and the optical distortion information DB 26a in the same way as the optical distortion correcting unit 22L, with respect to each of the visible light images generated from the captured image signal gL and the captured image signal gR (the visible light image of the left eye side, the visible light image of the right eye side).

In the outline image generation process, the outline images of the operation tools J are generated with respect to each of the left eye side and the right eye side, on the basis of the information of the operation tool regions Aj of the left eye side and the right eye side detected in the operation tool detection process. In the superimposition process, the outline image of the left eye side generated in the outline image generation process is superimposed on the visible light image of the left eye side, and the outline image of the right eye side is superimposed on the visible light image of the right eye side, respectively. Thereby, the left eye image GL and the right eye image GR are obtained.

Note that the superimposition process can be performed before executing the optical distortion correction process.

(1-5. Conclusion and Effect)

As described above, when the captured images obtained by capturing the operation tool J (the object) that is transparent for a visible light (the light of the first wavelength band) and is opaque for an infrared light (the light of the second wavelength band) are the visible light image (the first captured image) which is the captured image obtained by selectively receiving the visible light and the infrared light image (the second captured image) which is the captured image obtained by selectively receiving the infrared light, the signal processing unit 16 (image processing device) of the first embodiment includes the operation tool detection processing unit 24L (target detecting unit) that detects the image region in which the operation tool J exists as the operation tool region Aj (the target region) on the basis of the infrared light image, and the superimposition processing unit 23L (outline superimposing unit) that superimposes the outline of the operation tool J on the visible light image on the basis of the information of the operation tool region Aj detected by the operation tool detection processing unit 24L.

As described above, a captured image in which the deeper side of the operation tool J is visually confirmable and the position of the operation tool J is visually confirmable is obtained by superimposing the outline of the operation tool J on the visible light image. Thus, the work efficiency of the surgical operation work performed using the transparent operation tool J is improved to improve the easiness of the surgical operation, in order to perform a safer surgical operation.

Also, the signal processing unit 16 of the first embodiment includes the optical distortion correction processing unit 22L (optical distortion correcting unit) that corrects the optical distortion generated by the operation tool J with respect to the operation tool region Aj in the visible light image. Thereby, the optical distortion generated in the operation tool region Aj in the visible light image is corrected. Thus, the visibility of the object (the intracorporeal object X) that is positioned at the deeper side of the operation tool J is improved more.

Further, in the signal processing unit 16 of the first embodiment, the operation tool detection processing unit 24L identifies the type of the operation tool J on the basis of the infrared light image, and the optical distortion correction processing unit 22L corrects the optical distortion with the correction characteristic according to the type of the operation tool J identified by the operation tool detection processing unit 24L. Thereby, the optical distortion correction is performed with the appropriate correction characteristic according to the type of the operation tool J. Thus, the visibility of the object positioned at the deeper side of the operation tool J is improved, regardless of the type of the operation tool J.

<2. Second Embodiment>
(2-1. Configuration and Operation)

Figure 8:
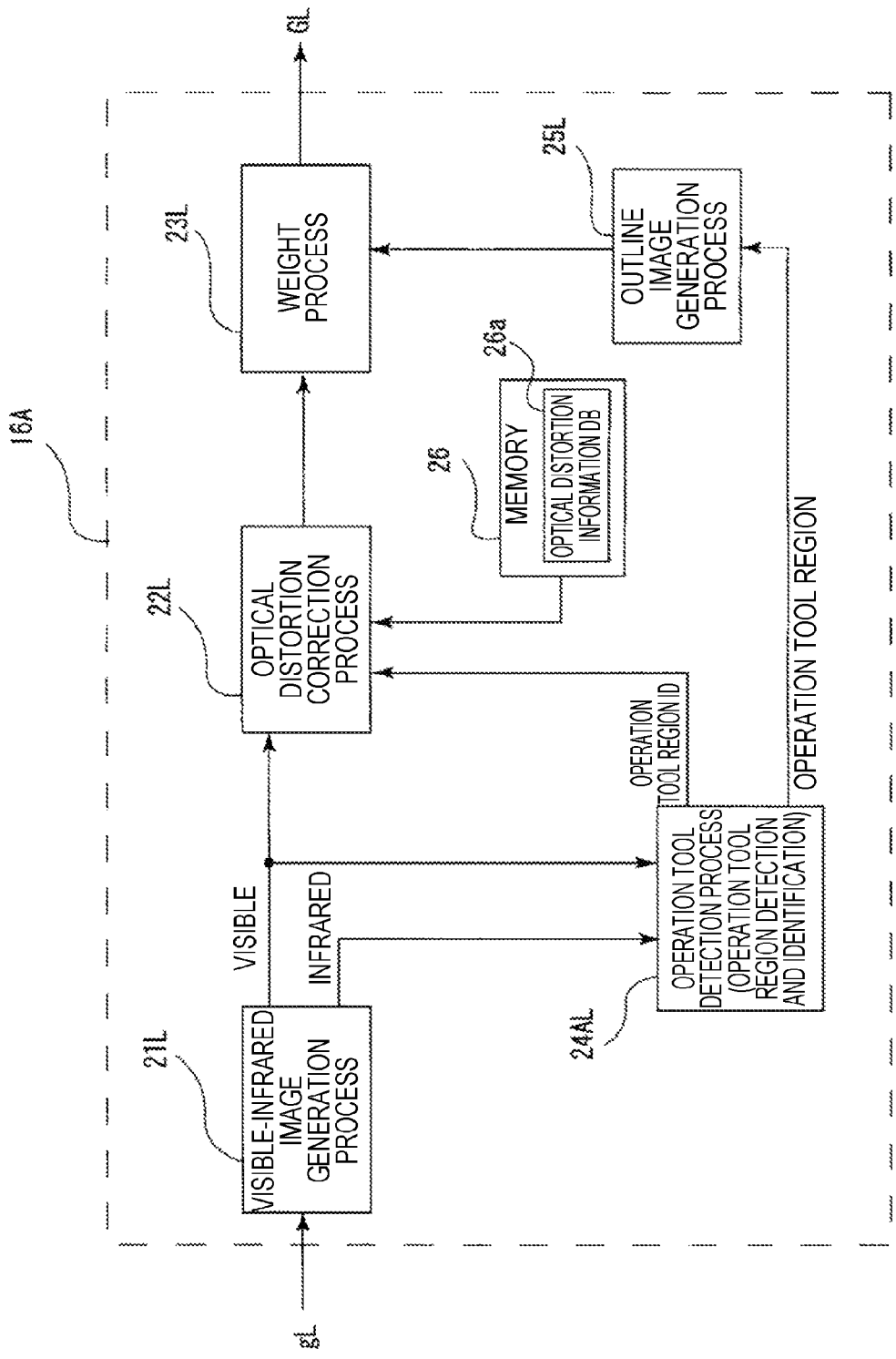
FIG. 8 is a block diagram for describing an inner configuration of an image capturing device of a second embodiment.

FIG. 8 is a block diagram for describing an inner configuration of an image capturing device of the second embodiment. Note that the image capturing device of the second embodiment is different from the image capturing device 1 of the first embodiment merely in having a signal processing device 16A instead of the signal processing unit 16, and the configuration of other parts is same. Hence, FIG. 8 illustrates only the inner configuration of the signal processing unit 16A. In the second embodiment as well, the configuration associated with the generation of the right side image GR is same as the configuration associated with the generation of the left eye image GL, and thus only the configuration associated with the generation of the left eye image GL is illustrated here to avoid a repetitive description. In the following description, the same parts as the parts that have already described are denoted with the same reference signs, and their description will be omitted.

The signal processing unit 16A is different from the signal processing unit 16 in having an operation tool detection processing unit 24AL instead of the operation tool detection processing unit 24L. Not only the infrared light image generated by the visible-infrared image generation processing unit 21L but also the visible light image is input into the operation tool detection processing unit 24AL. The operation tool detection processing unit 24AL performs the detection of the operation tool region Aj and the identification of the type of the operation tool J on the basis of the infrared light image and the visible light image.

Specifically, the operation tool detection processing unit 24AL generates an edge image (hereinafter, represented by "infrared edge image Gir") based on the infrared light image and an edge image (hereinafter, represented by "visible edge image Gv") based on the visible light image by performing the edge extraction with respect to each of the infrared light image and the visible light image. Thereafter, template matching using the templates of operation tools J is performed in the same way as the first embodiment with respect to each of the infrared edge image Gir and the visible edge image Gv. Then, the image regions that are detected by the template matching for the infrared edge image Gir and do not overlap with the image regions detected by the template matching for the visible edge image Gv are detected as the operation tool regions Aj.

Here, the operation tool J is opaque for the infrared light, and thus the operation tool region Aj can certainly be detected on the basis of the infrared light image only as in the first embodiment. However, the possibility that a part other than the operation tool J which has a similar shape to the operation tool J in the infrared light image is displayed is not nil, depending on the type of the intracorporeal object X as the subject and the image capturing environment for example, and it can be supposed that the part other than the operation tool J is erroneously detected as the operation tool region Aj if the detection of the operation tool region Aj is performed by the template matching on the basis of the infrared light image only.

Figure 9:
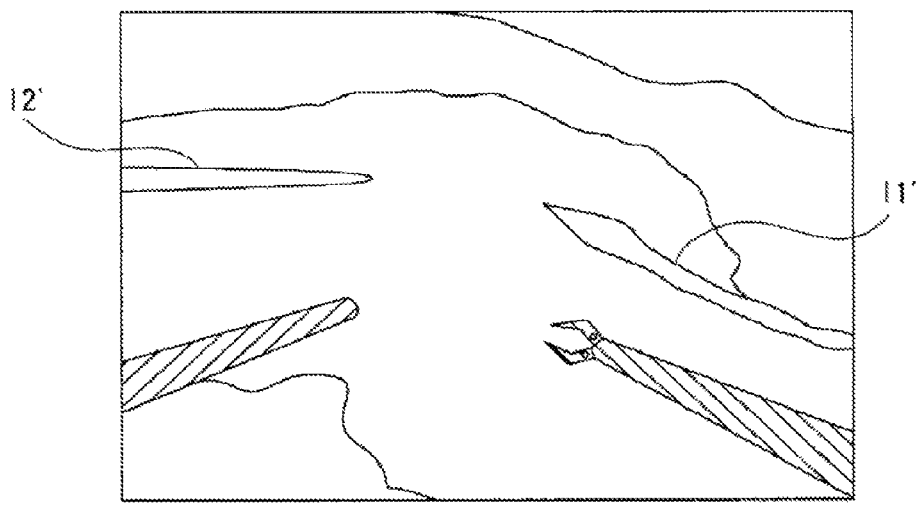
FIG. 9 is an explanatory diagram of meaning of detecting an operation tool region, using both of an infrared light image and a visible light image.
Figure 9:
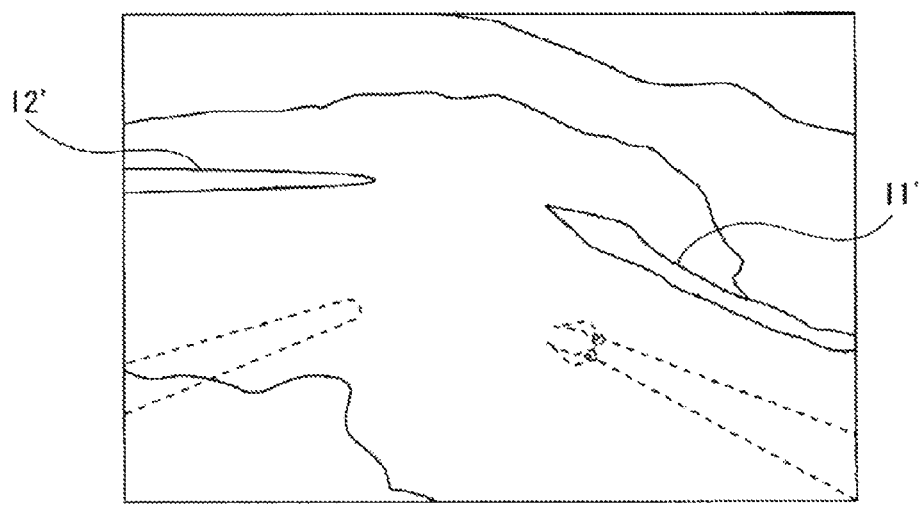

Thus, in the second embodiment, the detection of the operation tool region Aj is performed by using the visible light image as well, as described above. FIG. 9 is explanatory diagrams of meaning of detecting the operation tool region Aj using both of the infrared light image and the visible light image, and FIG. 9A illustrates the infrared edge image Gir, and FIG. 9B illustrates the visible edge image Gv. As illustrated in FIG. 9A, in the infrared edge image Gir of this case, the operation tools J (in the drawing, the hatched line areas) and the parts (in the drawing, "I1" I2") other than the operation tools J which have similar shapes to the operation tools J are displayed. In this case, if the template matching is performed for the infrared edge image Gir, these both image regions are detected as the operation tool regions Aj. Note that the parts other than the operation tools J I1', I2' which have the similar shapes to the operation tools J are not parts that are opaque for the infrared light like the operation tools J, and thus displayed not only in the infrared light image side but also in the visible light image side with a high possibility (refer to FIG. 9B). On the other hand, the operation tools J are transparent for the visible light, and thus the image regions in which the operation tools J exist are not detected by the template matching performed for the visible edge image Gv. Thus, if the template matching is performed with respect to the visible edge image Gv of this case, only the image regions of the parts I1', I2' are detected with a high possibility.

In consideration of this point, in the second embodiment, as described above, the image regions that are detected by the template matching for the infrared edge image Gir and do not overlap with the image regions detected by the template matching for the visible edge image Gv are detected as the operation tool regions Aj. Thereby, the detection accuracy of the operation tool regions Aj can be improved.

Here, in the present example, the visible light image is a color image, and thus can be said to be an image of respective colors of red, green, and blue. In this case, it is possible that the parts I1', I2' are displayed in the image of a certain color but are not displayed in the images of other colors. Thus, the template matching of the visible light image side is performed for the images of a plurality of colors. Specifically, in the present example, the red edge image Gvr, the green edge image Gvg, and the blue edge image Gvb are generated based on the red image, the green image, and the blue image by performing the edge extraction with respect to the red image, the green image, and the blue image respectively, and the template matching using the templates of the operation tools J is performed for each of the red edge image Gvr, the green edge image Gvg, and the blue edge image Gvb. Then, the image regions that are detected by the template matching for the infrared edge image Gir and do not overlap with any of the image regions detected by the template matching for the red edge image Gvr, the green edge image Gvg, and the blue edge image Gvb are detected as the operation tool regions Aj.

The parts I1', I2' are detected more easily in the visible light image side, by performing the template matching with respect to the respective images obtained by selectively receiving the lights of the different wavelength bands of red, green, and blue in the visible light band. Thus, the detection accuracy of the operation tool regions Aj is improved more, by detecting, as the operation tool regions Aj, the image regions that does not overlap with the image regions detected in the template matching with respect to a plurality of images of these red, green, blue.

Although, in the above, the results of the template matching performed for all of the red image, the green image, and the blue image composing the visible light image are used, if a result of the template matching performed with respect to the images of at least two colors among these images of red, green, and blue is used, the parts I1', I2' are detected with a higher possibility than when the template matching is performed with respect to the image of one color, and the detection accuracy of the operation tool regions Aj can be improved.

Here, in the second embodiment as well, the identification of the types of the operation tools J is performed by linking operation tool IDs to the templates of the operation tools J in the same way as the first embodiment.

Note that the operation of the signal processing unit 16A described above can be performed by software in the same way as the first embodiment. In that case, the process of the operation tool detection processing unit 24AL described above may be executed as the operation tool detection process of step S102 illustrated in FIG. 7B.

(2-2. Conclusion and Effect)

As described above, in the signal processing unit 16A (the image processing device) of the second embodiment, the operation tool detection processing unit 24AL (the target detecting unit) detects the operation tool regions Aj (the target regions) on the basis of the infrared light image (the second captured image) and the visible light image (the first captured image). Thereby, the operation tool regions Aj are detected on the basis of the image that displays the operation tools J (the objects) transparently and the image that displays the operation tools J opaque. Thus, the detection accuracy of the operation tool regions Aj can be improved.

Also, in the signal processing unit 16A of the second embodiment, the operation tool detection processing unit 24AL generates the infrared edge image Gir (the second edge image) and the visible edge image Gv (the first edge image) by performing the edge extraction with respect to each of the infrared light image and the visible light image, and performs the template matching using the templates of the operation tools J for each of the infrared edge image Gir and the visible edge image Gv, and detects the image regions that are detected by the template matching for the infrared edge image Gir and do not overlap with the image regions detected by the template matching for the visible edge image Gv as the operation tool regions Aj. Thereby, the image regions that are erroneously detected in the template matching of the infrared light image side (the image region displaying the parts I1', I2') can be excluded. Thus, the detection accuracy of the operation tool regions Aj can be improved.

Further, in the signal processing unit 16A of the second embodiment, the operation tool detection processing unit 24AL generates the edge images (a plurality of first edge images) based on a plurality of images among the infrared edge image Gir (the second edge image), the red image, the green image, and the blue image, by performing the edge extraction with respect to a plurality of images among the infrared light image, the red image, the green image, and the blue image (a plurality of first captured images obtained by selectively receiving the respective lights of the different wavelength bands in the first wavelength band), and performs the template matching for each of the generated edge images, and detects, as the operation tool regions Aj, the image regions that are detected by the template matching for the infrared edge image Gir and do not overlap with any of the image regions detected by the template matching for the edge images based on a plurality of images among the red image, the green image, and the blue image. The parts (I1', I2') other than the operation tools J which have similar shapes to the operation tools J in the visible light image side is detected more easily, by performing the template matching with respect to a plurality of images among the red image, the green image, and the blue image. Thus, the detection accuracy of the operation tool regions Aj is improved more.

<3. Third Embodiment>

(3-1. Configuration and Operation)

Figure 10:
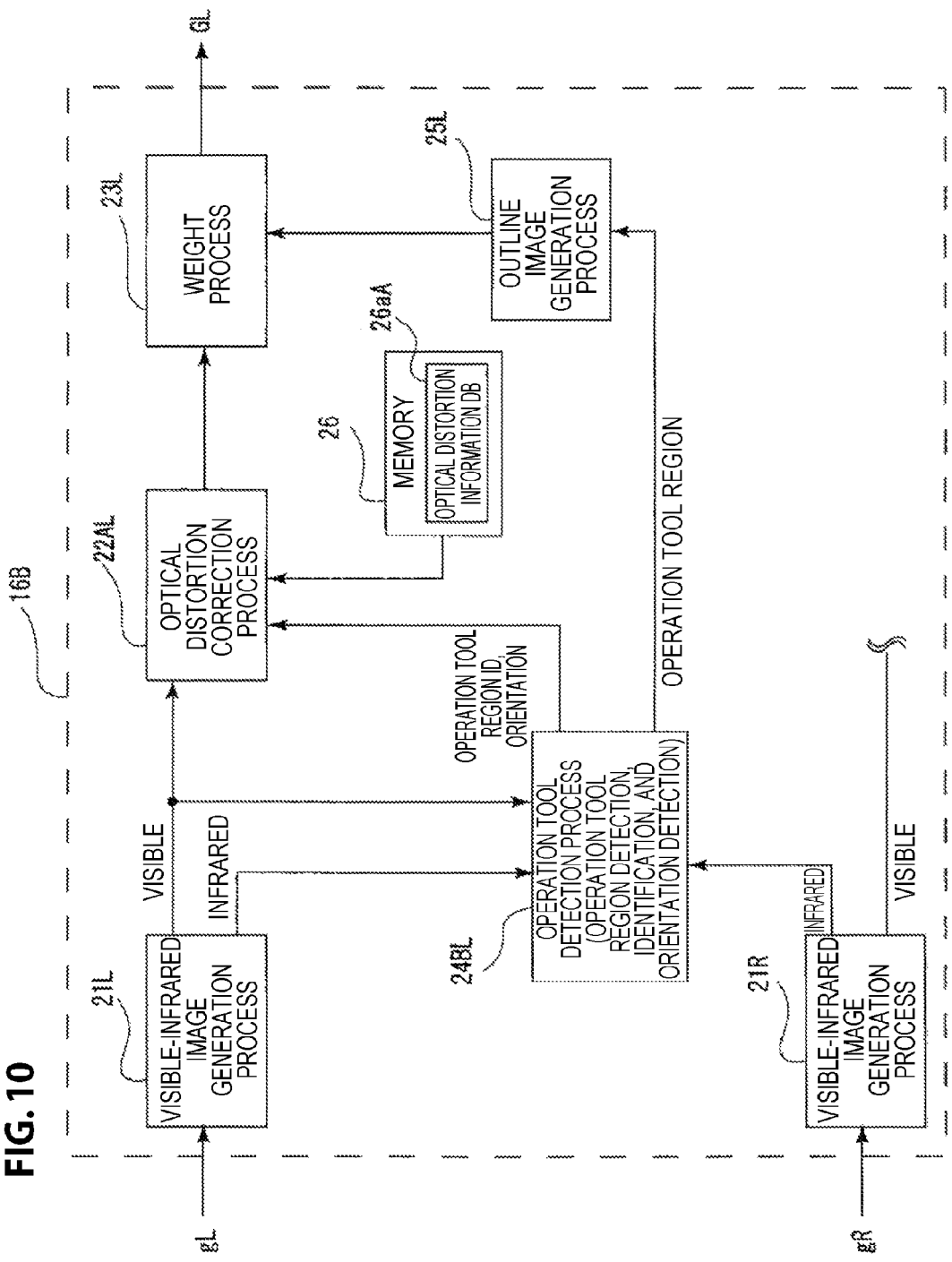
FIG. 10 is a block diagram for describing an inner configuration of an image capturing device of a third embodiment.

FIG. 10 is a block diagram for describing the inner configuration of the image capturing device of the third embodiment. Note that the image capturing device of the third embodiment is different from the image capturing device of the second embodiment merely in having a signal processing device 16B instead of the signal processing unit 16A, and the configuration of other parts is same. Hence, FIG. 10 illustrates only the inner configuration of the signal processing unit 16B. In the third embodiment as well, the configuration associated with the generation of the right side image GR is same as the configuration associated with the generation of the left eye image GL, and thus only the configuration associated with the generation of the left eye image GL is illustrated here (except for the visible-infrared image generation processing unit 21R) to avoid a repetitive description.

The signal processing unit 16B is different from the signal processing unit 16A in having an operation tool detection processing unit 24BL instead of the operation tool detection processing unit 24AL and an optical distortion correction processing unit 22AL instead of the optical distortion correction processing unit 22L, and in that the memory 26 does not store the optical distortion information DB 26a but the optical distortion information DB 26aA. As in the drawing, into the operation tool detection processing unit 24BL, the infrared light image and the visible light image generated by the visible-infrared image generation processing unit 21L are input, and the infrared light image generated by the visible-infrared image generation processing unit 21R is input. The visible-infrared image generation processing unit 21R generates the infrared light image and the visible light image by performing the same process as the visible-infrared image generation processing unit 21L with respect to the captured image signal gR. Note that, in the following, the infrared light image and the visible light image generated by the visible-infrared image generation processing unit 21L are represented by "left eye side infrared light image" and "left eye side visible light image", and the infrared light image and the visible light image generated by the visible-infrared image generation processing unit 21R, are represented by "right eye side infrared light image" and "right eye side the visible light image".

The operation tool detection processing unit 24BL performs the detection of the operation tool region Aj, the identification of the type of the operation tool J, and the detection of the orientation of the operation tool J. The detection of the operation tool region Aj and the identification of the type of the operation tool J are performed by the same method as the second embodiment, on the basis of the left eye side infrared light image and the left eye side visible light image. The information of the detected operation tool regions Aj is input into the outline image generation processing unit 25L and the optical distortion correction processing unit 22AL, and the information of the operation tool ID that represents the type of the operation tool J is input into the optical distortion correction processing unit 22AL.

The detection of the orientation of the operation tool J is performed by generating three-dimensional position information with respect to the operation tool J on the basis of the left eye side infrared light image and the right eye side infrared light image.

Figure 11:
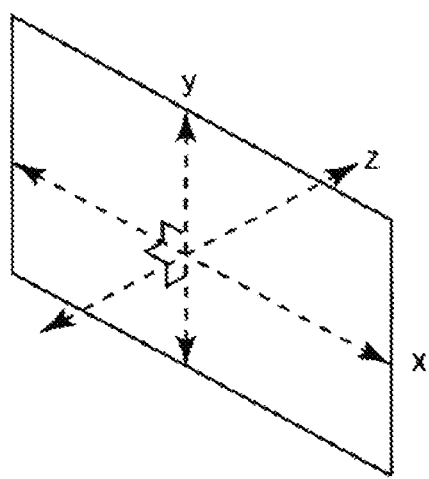
FIG. 11 is an explanatory diagram of three-dimensional position information.

FIG. 11 is an explanatory diagram of the three-dimensional position information. X axis and y axis in the drawing are axes having an orthogonal relationship in the plane in parallel with the imaging capturing surface of the image sensor 15-L. X axis is an axis in parallel with the horizontal direction of the image sensor 15-L, and y axis is an axis in parallel with the vertical direction of the image capturing device 15. Z axis is an axis orthogonal to a plane in parallel with the above imaging capturing surface. The three-dimensional position information is position information expressed by coordinates (x, y, z). That is, in the information, the position of the subject displayed in the image is expressed by the position (x, y) in the horizontal direction and the vertical direction in the image and the distance (z) to the subject in the real space.

The distance information to the subject is calculated from the value of the parallax generated between the image of the left eye side and the image of the right eye side. In the present example, the operation tool detection processing unit 24BL calculates the value of the parallax by what is called a corresponding point searching method. That is, image regions that are regarded as being the same points in the left eye side infrared light image and the right eye side infrared light image are detected as corresponding points, and the parallax is calculated for each corresponding point. Thereafter, the operation tool detection processing unit 24BL calculates the distance (z) from the calculated value of the parallax. That is, each of the values of parallax is converted to the distance (z) on the basis of information of the pixel pitch of the image sensor 15-L and the focal length of the left eye optical system 14-L and other information. As described above, the three-dimensional position information (x, y, z) is calculated for each corresponding point, by detecting the corresponding point of the left eye side infrared light image and the right eye side infrared light image and calculating the distance from the value of parallax for each corresponding point. A distance image (three-dimensional map, depth map) based on the infrared light image is obtained by calculating the three-dimensional position information.

The operation tool detection processing unit 24BL detects the orientation of the operation tool J, from the three-dimensional position information of the operation tool region Aj in the distance image acquired as described above. Here, the orientation means the slope of the three axes of x axis, y axis, and z axis. The information of the orientation detected by the operation tool detection processing unit 24BL is input into the optical distortion correction processing unit 22AL.

The optical distortion correction processing unit 22AL performs the optical distortion correction for the operation tool region Aj in the visible light image, on the basis of the optical distortion information DB 26aA and the information of the operation tool ID and the orientation input from the operation tool detection processing unit 24BL.

As illustrated in FIG. 12, in the optical distortion information DB 26aA, optical distortion characteristic information is associated with each combination of the operation tool ID and the orientation. In order to build the optical distortion information DB 26aA, the optical distortion characteristic information of each orientation is calculated for each type of the operation tool J as the optical distortion characteristic information, assuming that the operation tool J is a "lens". Then, the calculated optical distortion characteristic information is associated with each combination of the type (the operation tool ID) and the orientation of the operation tool J.

The optical distortion correction processing unit 22AL acquires the optical distortion characteristic information identified by the input operation tool ID and the orientation information among the optical distortion characteristic information stored in the optical distortion information DB 26aA, and performs the optical distortion correction for the operation tool region Aj in the visible light image on the basis of the acquired optical distortion characteristic information. That is, the correction is performed to cancel the optical distortion. Thereby, the optical distortion correction is performed with the correction characteristic according to the type and the orientation of the operation tool J.

Note that the operation of the signal processing device 16B described above is also performed by software in the same way as the first embodiment. In that case, the optical distortion information DB 26aA is stored in the memory 27 illustrated in FIG. 7A. Then, it may be such that the process of the operation tool detection processing unit 24BL described above is executed as the operation tool detection process of step S102 illustrated in FIG. 7B, and the process of the optical distortion correction processing unit 22AL described above is executed as the optical distortion correction process of step S103.

(3-2. Conclusion and Effect)

As described above, in the signal processing unit 16B (the image processing device) of the third embodiment, the operation tool detection processing unit 24BL (the target detecting unit) generates the three-dimensional position information of the operation tool J (the object) on the basis of the left eye side infrared light image (the left eye side second captured image) and the right eye side infrared light image (the right eye side second captured image), and detects the orientation of the operation tool J on the basis of the three-dimensional position information. Then, the optical distortion correction processing unit 22AL (the optical distortion correcting unit) corrects the optical distortion with the correction characteristic according to the orientation of the operation tool J detected by the operation tool detection processing unit 24BL. Thereby, the optical distortion correction is performed by an appropriate correction characteristic according to the orientation of the operation tool J. Thus, the visibility of the object positioned at the deeper side of the operation tool J is improved, regardless of the orientation of the operation tool J.

<4. Exemplary Variant>

Note that the present technology is not limited to the specific examples described above, but various exemplary variants are conceived. For example, although in the above example the operation tool region Aj is detected by template matching, the operation tool region Aj may be detected on the basis of the distance information calculated on the basis of the parallax between the left eye side infrared light image and the right eye side infrared light image. During a surgical operation, the operation tool J is positioned at the front side of the intracorporeal object X at a normal time. This point is utilized to detect the operation tool region Aj from the distance information. For example, there is a method that detects an image region at which the distance is within a predetermined range in the aforementioned distance image (the three-dimensional map), as the operation tool region Aj. As described above, the operation tool region Aj can be detected by using the distance information.

Here, the detection accuracy of the operation tool region Aj is improved by using the distance information in conjunction with the detection by the template matching. Specifically, there is a method in which the image regions having a similar shape to the operation tool J are detected by performing the template matching described in the first embodiment and the second embodiment, and only the image region whose distance is within a predetermined range is detected as the operation tool region Aj. Thereby, the detection accuracy of the operation tool region Aj can be improved more than when the detection is performed by the template matching only.

Also, as the detection method of the operation tool region Aj using the distance information, there is a method in which the distance image is generated with respect to each of the infrared light image and the visible light image, and the difference is obtained between those distance images. Specifically, the distance image is generated with respect to each of the infrared light image and the visible light image, and the difference image is generated between the distance image of the infrared light image and the distance image of the visible light image, and the operation tool region Aj is detected on the basis of the difference image. The operation tool J is displayed only in the infrared light image, and is not displayed in the visible light image. Also, the operation tool J is positioned at more front side than other subjects. Because of this point, only the image region in which the operation tool J exists is extracted in the difference image, by generating the difference image between the distance image of the infrared light image and the distance image of the visible light image, as described above. Thus, the operation tool region Aj is detected properly on the basis of the difference image.

Also, although, in the above, a case has been illustrated in which the result of the detection of the operation tool region Aj performed for each frame image is sequentially output to the outline image generation processing unit 25L, in other words, is output as information used in the outline superimposition of the operation tool J, alternatively the operation tool region Aj used in the superimposition of the outline may be decided on the basis of the result of the detection of the operation tool region Aj performed for a plurality of frame images. For example, the operation tool region Aj that is detected a plurality of times in a row as a result of the detection of the operation tool region Aj performed for a plurality of frame images is output as the information of the operation tool region Aj used in the superimposition of the outline. Thereby, even if a part displaying an object other than the operation tool J is erroneously detected as the operation tool region Aj due to influence such as temporary noise, the influence is not reflected in the outline superimposition. Thus, the outline image of the operation tool J is displayed correctly.

Also, although, in the above, a case has been illustrated in which the detection of the operation tool region Aj by the template matching is performed on the basis of the shape of the operation tool J as a criterion, but the criterion may be other feature points such as change of the color of the operation tool J, or the detection may be performed on the basis of both of the shape and another feature point as a criterion.

Further, although, in the above, the image after the edge extraction is used in the detection of the operation tool region Aj, performing the edge extraction is non-essential. For example, as an example of the detection using the infrared light image only, there is a method in which the part having a brightness value that is larger (or smaller) than a predetermined value is detected as the operation tool region Aj. This is a preferable method, when the operation tool J of a large reflectance (or absorptance) for the infrared light is used. That is, if the reflectance (or the absorptance) for the infrared light is large (or small), the pixel value of the part displaying the operation tool J is large (or small) significantly. Thus, the operation tool region Aj can be detected by the above detection method.

Alternatively, as a method that does not perform the edge extraction, there is a detection method based on the difference image between the infrared light image and the visible light image. Between the infrared light image and the visible light image, the difference between image patterns is large in parts where the operation tool J exists, and the difference between image patterns is small in other parts. Hence, in the difference image between the infrared light image and the visible light image, the brightness value (the difference value) is large in the parts where the operation tool J exists, and the brightness value is small in the other parts. That is, the part where the operation tool J exists is emphasized in the difference image between the infrared light image and the visible light image. Thus, if the emphasized part is extracted, that is, if the image region having a brightness value that is equal to or larger than a predetermined value in the difference image is extracted, the operation tool region Aj can be detected.

Also, although, in the above, a case has been illustrated in which the infrared light (the light of the second wavelength band) and the visible light (the light of the first wavelength band) are received by the same image sensor (15-L or 15-R), the lights may be received by different image sensors. That is, the image sensor for generating the infrared light image and the image sensor for generating the visible light image may be provided separately.

Also, although, in the above, an example has been illustrated in which the infrared light and the visible light are received simultaneously by the same image sensor, the infrared light and the visible light may be received in a time-sharing manner. In that case, an image sensor including arrayed pixels formed with wavelength filters that transmit the red light and the infrared light, pixels formed with the wavelength filters that transmit the green light and the infrared light, and pixels formed with the wavelength filters that transmit the blue light and the infrared light is used. In addition, the light emission of the visible light by the first light source 11-1 and the light emission of the infrared light by the second light source 11-2 are performed alternatingly, and the image sensor acquires the captured image signal separately during the light emission period of the visible light and the light emission period of the infrared light. Thereby, the visible light image and the infrared light image are acquired in a time-sharing manner. In the above time-sharing acquisition method, the infrared light is received at each pixel of the image sensor, and thus the interpolation process can be omitted in the generation of the infrared light image.

Also, although, in the above, a case has been illustrated in which the optical distortion correction is performed with the correction characteristic according to the type and the orientation of the operation tool J, the optical distortion correction may be performed with the correction characteristic according to the distance. Specifically, the correction characteristic (the inverse function of the optical distortion characteristic information) is calibrated according to the distance of the detected operation tool region Aj, and the optical distortion correction is performed for the operation tool region Aj with the correction characteristic after the calibration. Thereby, the optical distortion correction is performed with the appropriate correction characteristic according to the distance of the operation tool J. Thus, the visibility of the object that is positioned at the deeper side of the operation tool J is improved, regardless of the distance of the operation tool J.

Also, although, in the above, a case has been illustrated in which the outline superimposition and the optical distortion correction are performed for the operation tool J, the present technology can be preferably applied to a case in which the outline superimposition and the optical distortion correction are performed for other objects other than the operation tool. The objects other than the operation tool are, for example, objects handled by the operation tool during the surgical operation, such as artificial blood vessel and bone, for example. When the present technology is applied to a case in which other objects other than the operation tool are used, the work efficiency can be improved with respect to the work using the transparent object.

Also, although, in the above, a case has been illustrated in which both of the outline superimposition and the optical distortion correction of the operation tool J are performed, the configuration may be such that only the optical distortion correction is performed, and the outline superimposition is not performed.

Note that the effects described in the present specification are only illustrative and are not restrictive, and other effects may also be performed.

<5. Present Technology>

Additionally, the present technology may also be configured as below.

(1)
An image processing device including:
a target detecting unit configured to detect an image region where an object exists as a target region on the basis of a second captured image, when a first captured image is a captured image obtained by selectively receiving a light of a first wavelength band, and the second captured image is a captured image obtained by selectively receiving a light of a second wavelength band, the captured images being obtained by capturing the object that is transparent for the light of the first wavelength band and is opaque for the light of the second wavelength band; and
an outline superimposing unit configured to superimpose an outline of the object on the first captured image on the basis of information of the target region detected by the target detecting unit.

(2)
The image processing device according to (1), wherein
the target detecting unit detects the target region on the basis of the second captured image and the first captured image.

(3)
The image processing device according to (1) or (2), wherein
the target detecting unit
generates a second edge image based on the second captured image and a first edge image based on the first captured image by performing an edge extraction with respect to each of the second captured image and the first captured image,
performs a template matching using a template of the object for each of the second edge image and the first edge image, and
detects, as the target region, an image region that is detected by the template matching for the second edge image and does not overlap with an image region detected by the template matching for the first edge image.

(4)
The image processing device according to (3), wherein
the target detecting unit
performs the edge extraction with respect to the second captured image and a plurality of first captured images obtained by selectively receiving lights of different wavelength bands in the first wavelength band, and generates the second edge image based on the second captured image and a plurality of first edge images based on the plurality of first captured images,
performs the template matching for each of the generated edge images, and
detects, as the target region, an image region that is detected by the template matching for the second edge image and does not overlap with any one of image regions detected by the template matching for the plurality of first edge images.

(5)
The image processing device according to any of (1) to (4), wherein,
when a left eye side second captured image and a right eye side second captured image are a left eye image and a right eye image obtained by stereoscopically capturing images of the object by means of an image sensor that selectively receives a light of the second wavelength band, respectively, the target detecting unit detects the target region on the basis of distance information calculated on the basis of a parallax between the left eye side second captured image and the right eye side second captured image.

(6)
The image processing device according to (5), wherein
the target detecting unit generates a distance image of the second captured image and a distance image of the first captured image on the basis of the distance information calculated with respect to each of the second captured image and the first captured image, generates a difference image between the distance image of the second captured image and the distance image of the first captured image, and detects the target region on the basis of the difference image.

(7)

The image processing device according to any of (1) to (6), wherein the target detecting unit decides the target region used in superimposition of the outline by the outline superimposing unit, on the basis of a detection result of the target region with respect to a plurality of frame images.

(8)

The image processing device according to any of (1) to (7), including:

an optical distortion correcting unit configured to correct an optical distortion generated by the object with respect to the target region in the first captured image.

(9)

The image processing device according to (8), wherein the target detecting unit identifies a type of the object on the basis of the second captured image, and the optical distortion correcting unit corrects the optical distortion with a correction characteristic according to the type of the object identified by the target detecting unit.

(10)

The image processing device according to (8) or (9), wherein, when a left eye side second captured image and a right eye side second captured image are a left eye image and a right eye image obtained by stereoscopically capturing images of the object by means of an image sensor that selectively receives a light of the second wavelength band, respectively, the target detecting unit generates three-dimensional position information of the object on the basis of the left eye side second captured image and the right eye side second captured image, and detects an orientation of the object on the basis of the three-dimensional position information, and the optical distortion correcting unit corrects the optical distortion with a correction characteristic according to the orientation of the object detected by the target detecting unit.

(11)

The image processing device according to (10), wherein the optical distortion correcting unit corrects the optical distortion with a correction characteristic according to a distance of the object.

REFERENCE SIGNS LIST 1 image capturing device
1a rigid endoscope
1b main body
J1, J2 operation tool
16, 16', 16A, 16B signal processing unit
22L, 22AL optical distortion correction processing unit
23L superimposition processing unit
24L, 24AL, 24BL operation tool detection processing unit
25L outline image generation processing unit
26, 27 memory
26a, 26aA optical distortion information database (DB)

The invention claimed is:

1. An image processing device comprising:
processing circuitry configured to
detect an image region where an object exists as a target region on the basis of a second captured image, when a first captured image is a captured image obtained by selectively receiving a light of a first wavelength band, and the second captured image is a captured image obtained by selectively receiving a light of a second wavelength band, the captured images being obtained by capturing the object that is transparent for the light of the first wavelength band and is opaque for the light of the second wavelength band; and
superimpose an outline of the object on the first captured image on the basis of information of the target region.

2. The image processing device according to claim 1, wherein
the processing circuitry detects the target region on the basis of the second captured image and the first captured image.

3. The image processing device according to claim 1, wherein
the processing circuitry
generates a second edge image based on the second captured image and a first edge image based on the first captured image by performing an edge extraction with respect to each of the second captured image and the first captured image,
performs a template matching using a template of the object for each of the second edge image and the first edge image, and
detects, as the target region, an image region that is detected by the template matching for the second edge image and does not overlap with an image region detected by the template matching for the first edge image.

4. The image processing device according to claim 3, wherein
the processing circuitry
performs the edge extraction with respect to the second captured image and a plurality of first captured images obtained by selectively receiving lights of different wavelength bands in the first wavelength band, and generates the second edge image based on the second captured image and a plurality of first edge images based on the plurality of first captured images,
performs the template matching for each of the generated edge images, and
detects, as the target region, an image region that is detected by the template matching for the second edge image and does not overlap with any one of image regions detected by the template matching for the plurality of first edge images.

5. The image processing device according to claim 1, wherein,
when a left eye side second captured image and a right eye side second captured image are a left eye image and a right eye image obtained by stereoscopically capturing images of the object by means of an image sensor that selectively receives a light of the second wavelength band, respectively, the processing circuitry detects the target region on the basis of distance information calculated on the basis of a parallax between the left eye side second captured image and the right eye side second captured image.

6. The image processing device according to claim 5, wherein
the processing circuitry generates a distance image of the second captured image and a distance image of the first captured image on the basis of the distance information calculated with respect to each of the second captured image and the first captured image, generates a difference image between the distance image of the second captured image and the distance image of the first captured image, and detects the target region on the basis of the difference image.

7. The image processing device according to claim 1, wherein
the processing circuitry decides the target region used in superimposition of the outline by the processing circuitry, on the basis of a detection result of the target region with respect to a plurality of frame images.

8. The image processing device according to claim 1, wherein
the processing circuitry is configured to correct an optical distortion generated by the object with respect to the target region in the first captured image.

9. The image processing device according to claim 8, wherein
the processing circuitry identifies a type of the object on the basis of the second captured image, and
the processing circuitry corrects the optical distortion with a correction characteristic according to the type of the object identified by processing circuitry.

10. The image processing device according to claim 8, wherein,
when a left eye side second captured image and a right eye side second captured image are a left eye image and a right eye image obtained by stereoscopically capturing images of the object by means of an image sensor that selectively receives a light of the second wavelength band, respectively,
the processing circuitry generates three-dimensional position information of the object on the basis of the left eye side second captured image and the right eye side second captured image, and detects an orientation of the object on the basis of the three-dimensional position information, and
the processing circuitry corrects the optical distortion with a correction characteristic according to the orientation of the object detected by the processing circuitry.

11. The image processing device according to claim 10, wherein
the processing circuitry corrects the optical distortion with a correction characteristic according to a distance of the object.

12. An image processing method comprising:
detecting, using processing circuitry, as a target region, an image region where an object exists on the basis of a second captured image, when a first captured image is a captured image obtained by selectively receiving a light of a first wavelength band, and the second captured image is a captured image obtained by selectively receiving a light of a second wavelength band, the captured images being obtained by capturing the object that is transparent for the light of the first wavelength band and is opaque for the light of the second wavelength band; and
superimposing an outline of the object on the first captured image on the basis of information of the target region.

13. A non-transitory computer readable medium including executable instructions, which when executed by a computer cause the computer to:
detect, as a target region, an image region where an object exists on the basis of a second captured image, when a first captured image is a captured image obtained by selectively receiving a light of a first wavelength band, and the second captured image is a captured image obtained by selectively receiving a light of a second wavelength band, the captured images being obtained by capturing the object that is transparent for the light of the first wavelength band and is opaque for the light of the second wavelength band; and
superimpose an outline of the object on the first captured image on the basis of information of the target region.

* * * * *